United States Patent [19]

Jerman et al.

[11] Patent Number: 4,471,647

[45] Date of Patent: Sep. 18, 1984

[54] GAS CHROMATOGRAPHY SYSTEM AND DETECTOR AND METHOD

[75] Inventors: John H. Jerman; Stephen C. Terry, both of Palo Alto, Calif.

[73] Assignee: Board of Regents of Stanford University, Palo Alto, Calif.

[21] Appl. No.: 360,414

[22] Filed: Mar. 22, 1982

Related U.S. Application Data

[63] Continuation of Ser. No. 141,269, Apr. 18, 1980, abandoned.

[51] Int. Cl.³ ............................................. G01N 27/18
[52] U.S. Cl. ......................................... 73/23; 73/23.1; 338/25; 374/135
[58] Field of Search ............... 73/23.1, 23, 27 R, 204; 374/35, 135; 338/22 R, 25, 34, 22 SD

[56] References Cited

U.S. PATENT DOCUMENTS

| | | | |
|---|---|---|---|
| 3,138,025 | 6/1964 | Fingerson | 374/35 |
| 3,138,948 | 6/1964 | Pfefferle | 73/27 R |
| 3,333,470 | 8/1967 | Fingerson | 73/27 R |
| 3,538,744 | 11/1970 | Karasek | 73/23.1 |
| 4,033,169 | 7/1977 | Fujishiro et al. | 73/23 |
| 4,142,400 | 3/1979 | Colla et al. | 73/23 |
| 4,213,335 | 7/1980 | Peter et al. | 73/204 |

OTHER PUBLICATIONS

K. Malin et al., "Mass Flow Meter", *IBM Technical Disclosure Bulletin*, vol. 21, No. 8, p. 3227, Jan. 1979.

G. C. Carle et al., "Microminiature Gas Chromatograph," NASA Tech. Brief B7210306, pp. 1 and 2, Sep. 1972.

S. C. Terry, "Gas Chromatography System Fabricated on Silicon Wafer Using Integrated Circuit Tech.," Stanford Electronics Lab, Tech. Report 4603-1, pp. 1-128, May 1975.

S. C. Terry et al., "Feasibility Study of Pocket-Sized Gas Chromatographic Air Analyzer," Stanford Electronics Lab, pp. 1-102, Jul. 1977.

Seiyama et al., "Study on a Detector for Gaseous Components Using Semiconductive Thin Films," *Anal. Chem.*, vol. 38, No. 8, pp. 1069-1072, Jul. 1966.

*Primary Examiner*—Stephen A. Kreitman
*Attorney, Agent, or Firm*—Flehr, Hohbach, Test, Albritton & Herbert

[57] ABSTRACT

There is described a gas chromatographic assembly formed on a semiconductor wafer by etching techniques. There is also described an improved thermal detector for use therewith.

6 Claims, 9 Drawing Figures

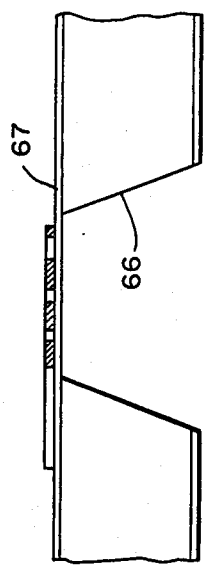
FIG.—3
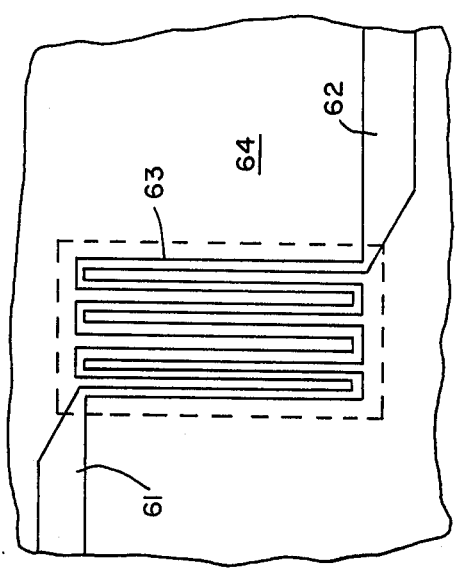
FIG.—4
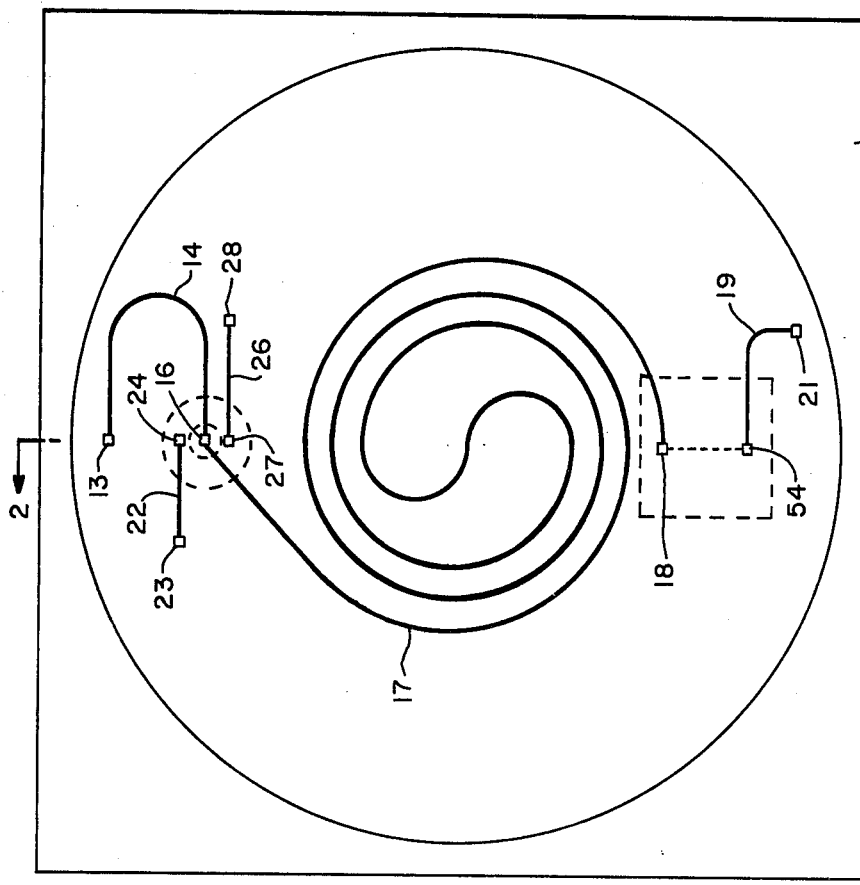
FIG.—1

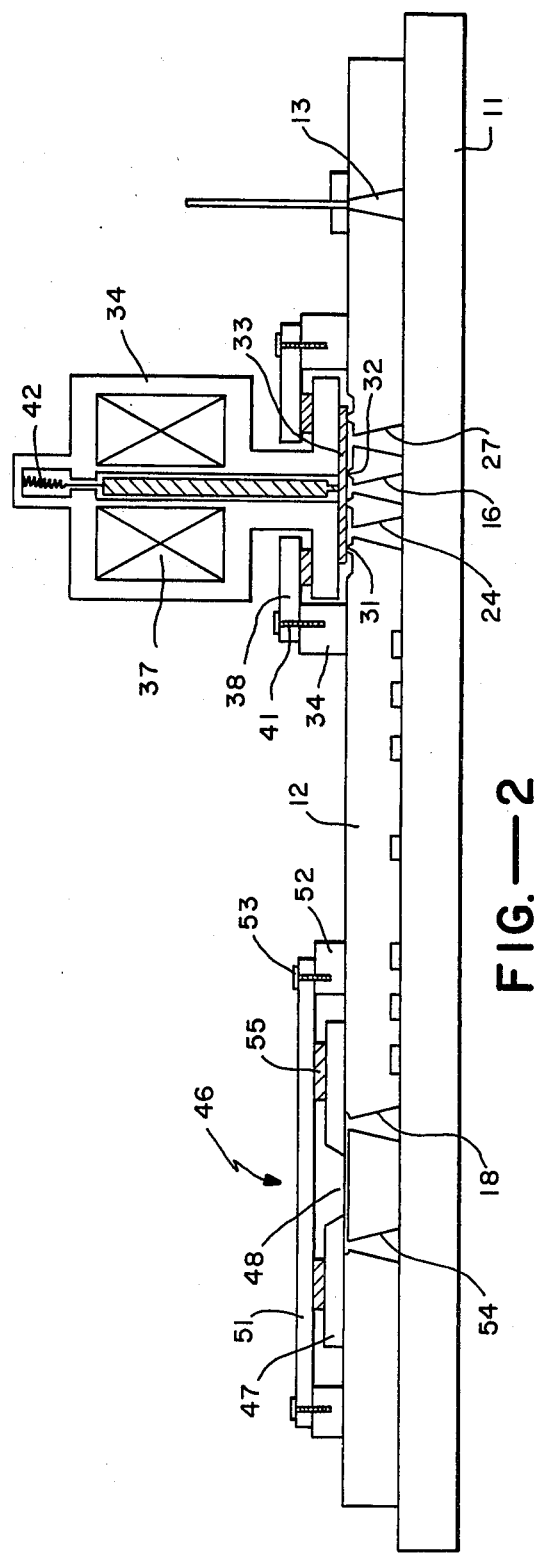
FIG.—2
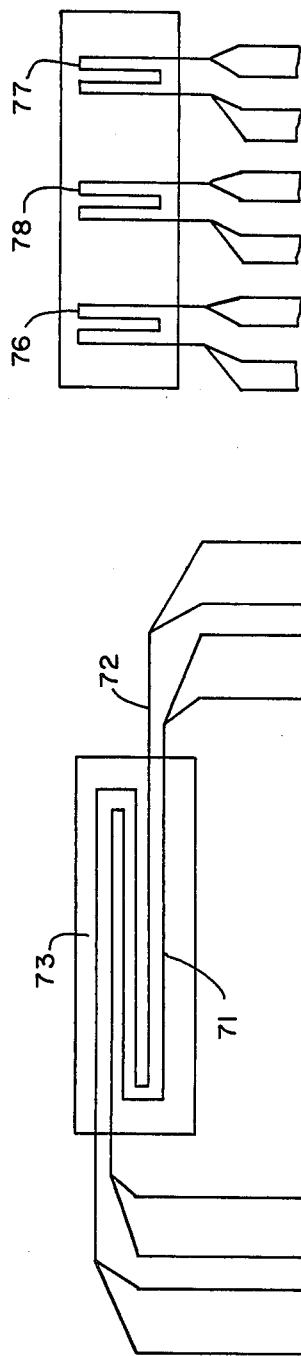
FIG.—6
FIG.—5

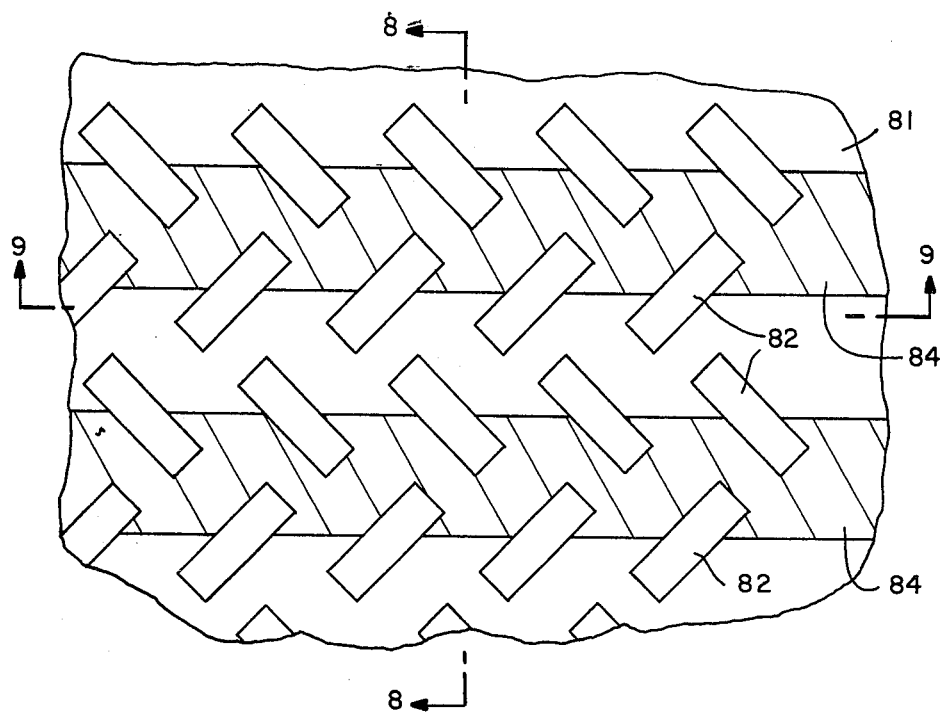
FIG.—7
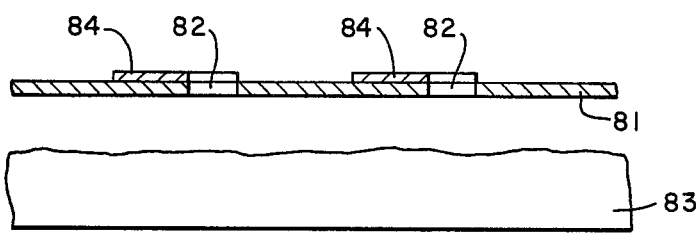
FIG.—8
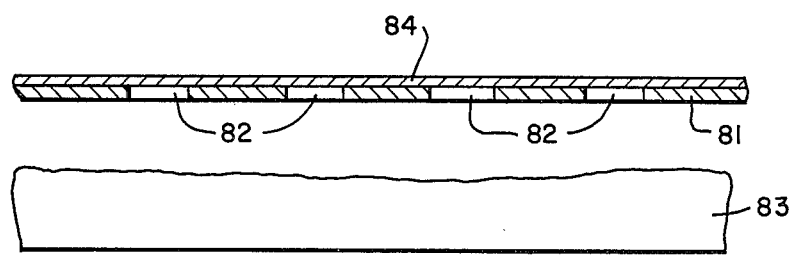
FIG.—9

GAS CHROMATOGRAPHY SYSTEM AND DETECTOR AND METHOD

The Government has rights in this invention persuant to Contract No. N10SH 210-77-0159.

This is a continuation, of application Ser. No. 141,269 filed Apr. 18, 1980, now abandoned.

This invention relates generally to a miniature gas chromatography system and more particularly to a thermal conductivity detector for use therein and to a method of making same.

In general, the gas chromatograph of the present invention has the same basic components as conventional gas chromatographs. More particularly, it includes a carrier gas supply, a sample injection system for injecting a sample gas into the carrier gas, a separation column where the components of the sample gas are separated, an output detector and an associated data analysis system. In the present invention, the capillary column, sample injection system and thermal conductivity detector are integrated on a single semiconductor wafer. The components are fabricated using chemical etching and photolithographic techniques whereby to provide a miniature assembly. The construction of such systems is suggested in NASA TECH BRIEF B72-10306, issued September 1972.

In the past, various types of detectors have been employed to detect the presence of the sample and its components. The detectors comprise either discrete thermistors or metal wire strung between support posts in a cavity at the output of the chromatograph. This method of construction is difficult to miniaturize due to the problems in assembling miniature elements and in controlling the placement of the elements in the output gas stream. In thermistor structures, it is additionally difficult to form discrete thermistors and associated lead wires with dimensions less than 100 micrometers. Discrete metal wires of very small diameter can be formed, but they are difficult to handle and to coil into miniature detectors.

The development of capillary gas chromatographs with very small column dimensions and correspondingly small gas flows has taxed the ability of conventional detectors. Any finite volume added by a detector has the property of diluting the output signals due to gas peaks in the chromatograph. This lowers the amplitude of the peaks and broadens them in time. Lower amplitude is undesirable since it can allow the signal to be lost in the noise. Peak broadening is undesirable since it can allow two adjacent output gas peaks to be merged, thus negating the separating capability of high resolution gas chromatography columns.

Thermal conductivity detectors operate by sensing temperature changes of the sensing element. Detectors with large, discrete sensing elements have significant thermal mass so that there is a finite thermal time constant in the detector response. Efficient and fast capillary columns have output peaks which are very narrow in time. Detector thermal time constants also have the effect of broadening the peaks and reducing the efficiency of the column. Thus, two important parameters for detectors for small diameter capillary column are low volume and small thermal mass.

It is an object of the present invention to provide an improved miniature gas chromatographic assembly including an input valve, capillary column and detector.

It is another object of the present invention to provide a detector assembly of small size, low dead volume, fast response and low power dissipation.

It is a further object of the present invention to provide a simple, low cost chromatographic assembly.

It is still a further object of the present invention to provide a low cost sensitive linear thermal conductivity detector.

The foregoing and other objects of the invention are achieved by a thermal detector which includes a thin film resistive element disposed on a membrane supported by a semiconductor substrate and to a method of making the same.

Other features of the invention are achieved in a gas chromatograph assembly comprising a wafer of semiconductor material including an elongated etched capillary groove, an etched carrier gas inlet groove having one end connected to one end of said capillary groove, a first feedthrough extending through the wafer and connected to the common ends of said capillary and carrier gas grooves, a gas inlet feedthrough cooperating with the other end of said etched carrier gas inlet groove, an etched sample gas inlet groove, second and third feedthroughs connected to the ends of said sample gas groove with said third feedthrough closely spaced to said first feedthrough, an etched exhaust groove, fourth and fifth feedthroughs connected to the end of said exhaust groove with said fourth feedthrough closely spaced from first feedthrough, valve means cooperating with said first, third and fourth feedthrough serving to selectively connect the carrier gas input groove and the exhaust groove to the first feedthrough, a sixth feedthrough at the other end of said capillary groove, a vent groove, seventh and eighth feedthrough connected to the ends of said vent groove with the seventh feedthrough spaced with respect to the sixth feedthrough, a plate cooperating with the grooved surface of said wafer to define carrier gas input, sample gas input and vent conduits and a capillary column, a thermal conductivity detector assembly comprising a thin film resistive means spaced from said wafer between said seventh and eighth feedthroughs to analyze the gases leaving the capillary column and means for directing the gas leaving the capillary column past the detector and to the vent groove. dr The invention will be more clearly understood from the following description taken in connection with the accompanying drawings of which:

FIG. 1 is a plan view of a gas chromatographic cell assembly;

FIG. 2 is a sectional view taken generally along the line 2—2 of FIG. 1;

FIG. 3 is an enlarged sectional view of a detector suitable for use in the system;

FIG. 4 is a plan view of the detector shown in FIG. 3;

FIG. 5 schematically shows another embodiment of detector and sensing element;

FIG. 6 shows still another embodiment;

FIG. 7 shows a further embodiment of the detector;

FIG. 8 is a sectional view taken generally along the line 8—8 of FIG. 7; and

FIG. 9 is a sectional view taken generally along the line 9—9 of FIG. 7.

Referring to FIGS. 1 and 2, the chromatographic sub-assembly is shown in detail. The sub-assembly comprises a suitable support such as a glass plate 11 which supports a thin wafer such as a silicon wafer 12 which is processed as will be presently described and which, in combination with the glass plate 11, forms the capillary passage for a gas chromatograph and passages for the introduction of carrier gas, sample gas and the like into the capillary path and past a suitable detector. More particularly, a carrier gas from a suitable source is introduced through an opening 13 formed through the wafer along an etched gas path 14 which is preferably of constricted diameter to thereby provide a high resistance gas path between the inlet opening 13 and through an opening 16 formed in the wafer to communicate with the upper side, the end of which is also in communication with the capillary path 17 formed by a spiral groove etched into the surface of the silicon substrate and having its other end communicating with an opening 18 extending upwardly through the silicon wafer. The wafer also includes a groove together with which the glass plate forms a vent passage 19 which communicates with the surrounds through opening 21.

In accordance with well known chromatography principles, sample gas is fed into the carrier gas stream periodically. The present apparatus includes a valve assembly and passages for introducing sample gas into the gas carrier passage at the point where the passage is connected to the capillary 17.

Referring more particularly to FIG. 1, there is provided a groove 22 which defines a passage between a sample gas input opening 23 formed through the wafer and its other end communicates with an opening 24 which extends through the wafer and feeds the gas upwardly to the surface of the wafer. A suitable vent passage 26 is formed by an etched groove and communicates at one end with an inlet opening 17 and its other end with an outlet opening 28 which extends through the wafer.

The openings 16, 24 and 27 communicate with an etched valve assembly. More particularly, the assembly includes a circular depression having two concentric circular ridges 31 and 32. The ridges cooperate with a valve diaphragm 33 secured to the solenoid housing 34 and actuated by a solenoid plunger 36 which is driven by a coil 37. The complete assembly is retained in cooperative relationship with this circular depression by means of a hold down plate 38 suitably attached to the upper surface of the silicon wafer as, for example, by means of a ring 39 and securing means 41. The plunger is spring loaded by means of a spring 42 whereby the valve diaphragm is normally pressed against the circular ridges closing off communication between the openings 16, 24 and 27. When a sample gas is to be introduced, the solenoid is activated lifting the plunger and diaphragm allowing the passages to intercommunicate whereby sample gas flows upwardly through the opening 24, downwardly through the passage 17 and through the capillary 17.

In accordance with the present invention, there is provided an improved detector assembly 46. The assembly comprises a silicon or other semiconductive wafer 47 which supports a diaphragm 48 onto which is formed a resistive element. The support 47 is etched away to provide a dead space for the heat transfer from the backside of the diaphragm 48. The complete assembly is clamped to the silicon wafer by means of a hold-down plate 51, ring 52 and securing means 53 together with a gasket 55. Thus, carrier gas and sample gas leaving the capillary tube through the opening 18 flows upwardly across the space between the diaphragm and the etched upper surface of the silicon wafer down through the opening 54 and out along the passage 19 to the outlet 21. As the gas travels in communication with the detector, the detector serves to detect the presence of the gas in a manner to be presently described.

Referring to FIGS. 3 and 4, the overall structure of a particular embodiment of the detector of the present invention is shown. This is the simplest version of the detector with only one sensing element. The wires for the external current source and the external voltage measuring device are connected to the bonding pads 61, 62 connected to opposite ends of the sensing element 63.

The sensing element 63 is a film resistor formed in a serpentine pattern formed by etching and supported by a thermally insulating support membrane 64, such as a Pyrex glass film. The metal paths to the bonding paths are substantially wider than in the sensing region so that a majority of the resistance of the sensor is over the central sensing region.

The serpentine geometry of the sensor is best seen in FIG. 4. The etched cavity 66 below the sensing element removes the thermally conductive semiconductor material from below the sensing region. The support membrane, in this case a Pyrex film, provides the mechanical support for the relatively thin metal film resistor. The resistor can be less than 1000 Å thick since the film need not have intrinsic mechanical strength. The cavity is formed by masking and etching the semiconductor support 47.

FIG. 5 shows one of the many alternate configurations of heating and sensing elements 71 and 72, respectively, on the support membrane 73. This configuration can be used to separate the heating and sensing functions. This can be done to separately optimize the resistance of the two devices or to electrically separate the heater power supply from the low noise sensing electronics. Two different materials could also be used as heating and sensing elements.

FIG. 6 shows an alternate arrangement. The detector arrangement includes two sensing elements 76, 77 arranged perpendicular to the direction of gas flow and on either side of a heating element 78. In this configuration the direction and magnitude of the gas flow can be determined by measuring the difference in temperature between sensor 76 and sensor 77.

FIG. 1, previously described, shows the mounting of the embodiment shown in FIGS. 3 and 4 on a particular miniature gas chromatograph. This miniature gas chromatograph (GC) is also fabricated in a silicon wafer 12 and with a Pyrex glass cover 11. This assembly is essentially similar in operation to conventional GC's and need not be described here. The output gas stream passes through a low volume feedthrough passage 14 in the substrate wafer to the detector channel. This channel is formed by the combination of an etched groove in the substrate wafer and the detector chip, which is mechanically clamped to the substrate wafer. The output gas stream passes over the detector sensing element, passes through another feedthrough passage 19, and passes eventually through a vent to the atmosphere. The detector chip thus forms one wall of the detector gas channel and does not contribute any appreciable dead volume to the detector region. The large majority of power dissipated by the sensing element passes through the carrier gas to the substrate wafer due to the relatively high thermal conductivity of the helium and hydrogen carrier gases normally used in gas chromatography. Thus, the thermal efficiency, the ratio of power dissipated through the carrier gas to the total dissipated power, of this structure is very high. Since the etch depths of these structures can be accurately controlled, the spacing of the sensing element to the substrate wafer can be made on the order of a few micrometers.

FIG. 7 shows a detailed view of the central sensor portion of another embodiment of a detector in accordance with the invention. In this structure the support membrane 81 is first etched in a number of places to produce a number of holes 82 in the membrane 81. The silicon 83 below the membrane, FIGS. 8 and 9, is then etched away through these holes until the support membrane is attached to the substrate only at the edges of the etched cavity. The sensing element 84 is situated on the support membrane above the etched cavity so that it is again thermally isolated from the detector substrate. FIGS. 8 and 9 show the etched cavity produced below the holes in the support membrane.

In the embodiment of FIGS. 7-9, the detector substrate can be clamped to form a detector channel in a similar manner as shown in FIG. 2. In this case, the gas both flows on top of the sensing element 84 but also flows in the etched cavity under the sensing element. The spaces between the holes in the support membrane can be adjusted so that there is rapid mixing of the gas in the detector channel and the etched cavity so that the etched cavity does not represent a dead volume in the detector region. This structure has the advantage of not having an immediate thermal path from the detector sensor to the ambient air, reducing the possibility of turbulence or other atmospheric disturbances from influencing the detector output.

Thus, there has been provided an improved detector assembly for gas chromatographic columns and an improved gas chromatograph assembly.

What is claimed is:

1. A gas chromatography assembly comprising:
   a wafer of semiconductor material including
      an elongated etched capillary groove;
      an etched carrier gas inlet groove having one end connected to one end of said capillary groove;
      a first feedthrough extending through the wafer and connected to the connected ends of said capillary and carrier gas grooves;
      a carrier gas inlet feedthrough connected to the other end of said inlet groove;
      an etched sample gas inlet groove;
      second and third feedthroughs connected to the ends of said sample gas groove with said third feedthrough closely spaced to said first feedthrough;
      an etched exchaust groove;
      fourth and fifth feedthroughs connected to the ends of said exhaust groove with said fourth feedthrough closely spaced to said first feedthrough;
      valve means cooperating with said first, third and fourth feedthroughs serving to selectively connect the sample gas input groove and the exhaust groove to the first feedthrough;
      a sixth feedthrough at the other end of said capillary groove;
      a vent groove;
      seventh and eighth feedthroughs connected to the ends of said vent groove with the seventh feedthrough spaced with respect to the sixth feedthrough;
   a plate cooperating with the grooved surface of said wafer to define carrier gas input, sample gas input and vent conduits and a capillary column;
   a thermal conductivity detector assembly comprising a thin metal film resistance means including a thin supporting membrane supported on a semiconductor support which includes a cavity behind the membrane mounted opposite and spaced from said wafer between said seventh and eight feedthroughs said supporting including openings which permit gas to flow on both sides of the membrane and a thin elongated metal film carried by said membrane; and
   means for directing the gas flowing from said capillary column past the detector to flow over both sides of the membrane to the vent groove.

2. A detector for use in connection with gas chromatographic apparatus comprising:
   an elongated metal film resistor, a membrane for supporting said metal film resistor said membrane having a plurality of holes permitting gas to flow on both sides of said membrane and means for supporting said membrane and film resistor.

3. Apparatus for use in temperature measurement comprising:
   a metal film resistor, a membrane for supporting said film resistor said membrane having a plurality of apertures, means for supporting said membrane and film resistor, and means for heating said film resistor.

4. A chromatography assembly comprising:
   a substrate body having at least one conduit therein for carrying a fluid;
   a thermal conductivity detector assembly, attached to said body, at one end of said one conduit;
   said detector assembly for measuring a certain property of the fluid flowing in said conduit past said detector assembly; and
   said assembly comprising at least one elongated metal film resistor, a membrane having a plurality of apperatures for supporting said membrane and film resistor, and means for supporting said membrane and film resistor such that said membrane is spaced from said body and said fluid is carried past both sides of said membrane, whereby said metal film is substantially thermally insulated by said fluid.

5. The assembly of claim 4 wherein said membrane supports a plurality of film resistors.

6. The assembly of claim 5 wherein one of said film resistors is for heating and another of said film resistors is for detecting the property of said fluid.

* * * * *